United States Patent
Maruta

[19]

[11] Patent Number: 5,980,462
[45] Date of Patent: Nov. 9, 1999

[54] ULTRASONIC DIAGNOSTIC DEVICES AND ULTRASONIC ENDOSCOPES

[75] Inventor: Koichi Maruta, Tanashi, Japan

[73] Assignee: Olympus Optical Co., Ltd., Japan

[21] Appl. No.: 09/179,268

[22] Filed: Oct. 27, 1998

[30] Foreign Application Priority Data

Nov. 10, 1997 [JP] Japan ................................ 9-307495

[51] Int. Cl.⁶ ..................................................... A61B 00/80
[52] U.S. Cl. ............................................................ 600/462
[58] Field of Search ................................... 600/454, 459,
600/461, 466, 467, 462, 471; 128/916

[56] References Cited

U.S. PATENT DOCUMENTS

| | | | |
|---|---|---|---|
| 4,466,444 | 8/1984 | Baba | 128/660 |
| 5,417,216 | 5/1995 | Tanaka | 600/459 |
| 5,467,779 | 11/1995 | Smith et al. | 600/462 |
| 5,497,776 | 3/1996 | Yamazaki et al. | 128/916 |

FOREIGN PATENT DOCUMENTS

| | | |
|---|---|---|
| 62-176436 | 8/1987 | Japan . |
| 62-231630 | 10/1987 | Japan . |
| 1-136638 | 5/1989 | Japan . |
| 4-82540 | 3/1992 | Japan . |
| 5-23337 | 2/1993 | Japan . |
| 7-289549 | 11/1995 | Japan . |

*Primary Examiner*—William E. Kamm
*Assistant Examiner*—Maulin Patel
*Attorney, Agent, or Firm*—Ostrolenk, Faber, Gerb & Soffen, LLP

[57] ABSTRACT

An ultrasonic diagnostic device of which forms two scanning planes includes an ultrasonic search unit at the tip of a long insertion part which conducts radial scanning by emitting ultrasonic waves in a direction vertical to the longitudinal axis direction of the insertion part, a reflector provided along with the ultrasonic search unit which reflects a part of the ultrasonic waves emitted from the ultrasonic search unit to the anterior direction of the insertion part, and a tip cap which covers the ultrasonic search unit and the reflector and is made of a material permeable to the ultrasonic waves emitted from the ultrasonic search unit.

27 Claims, 15 Drawing Sheets

FIG.3A
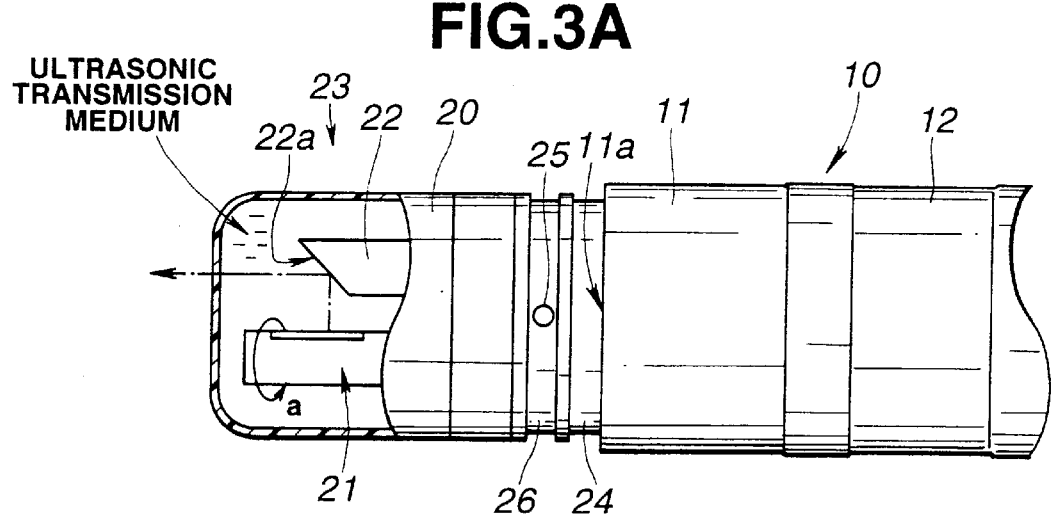
FIG.3B
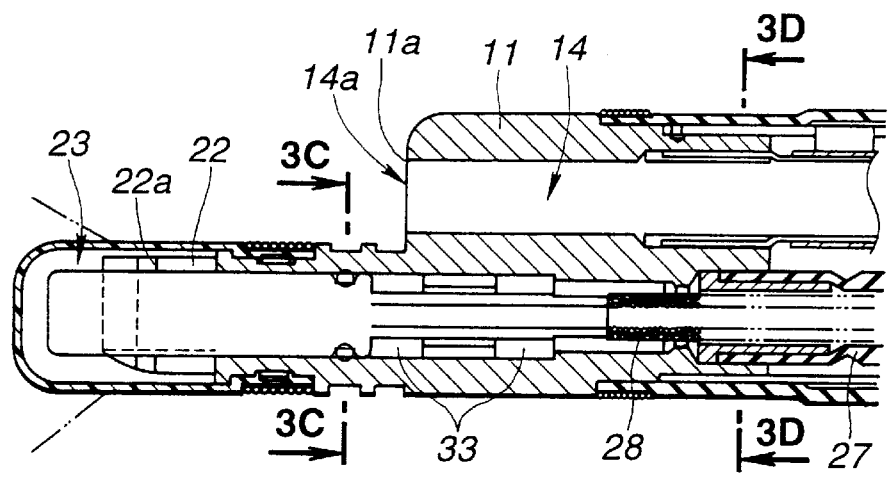
FIG.3C  FIG.3D
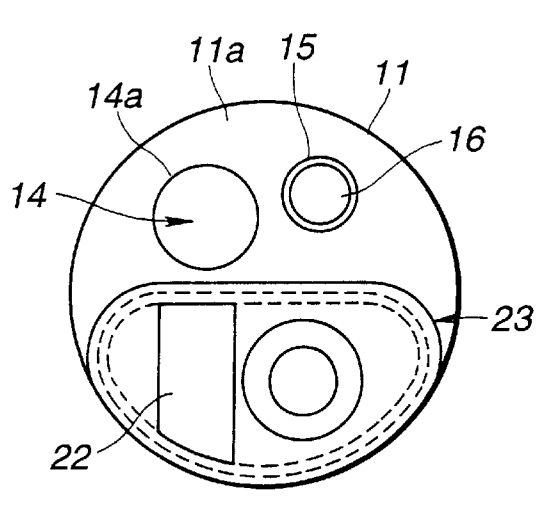
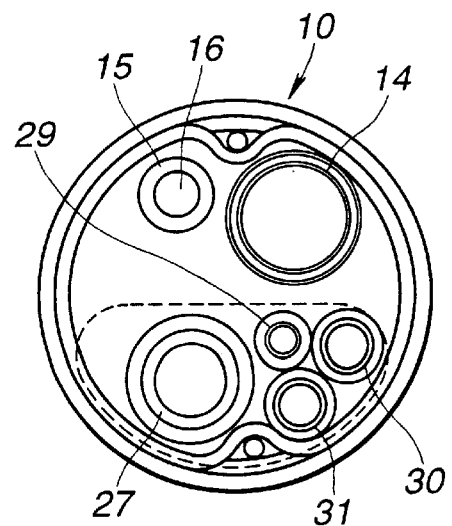

ULTRASONIC DIAGNOSTIC DEVICES AND ULTRASONIC ENDOSCOPES

BACKGROUND OF THE INVENTION

1. Field of the Invention

The present invention relates to ultrasonic diagnostic devices which possess an ultrasonic search unit of a radial scanning system.

2. Description of the Related Art

Endoscopes have been widely used for observations of organs within body cavities and a variety of therapeutic treatments using a treatment device inserted into a channel for passage as necessary.

With a type of endoscope having a channel for treatment device passage, ultrasonic diagnoses can be conducted by passing an ultrasonic probe into this channel, introducing it to an area to be diagnosed and then generating ultrasonic beams.

On the other hand, an ultrasonic probe having an ultrasonic search unit provided at the tip of an insertion part which is inserted into a body cavity and which enables ultrasonic tomograms to be obtained by the ultrasonic search unit has also been used. With the endoscope having a channel for treatment device passage in the insertion part, by protruding the treatment device through a delivery port at the tip of the channel, some treatments including collection of tissues with lesions and the like can be conducted.

There are several kinds of ultrasonic probes, including a radial scanning types to obtain ultrasonic tomograms in the lateral direction by scanning the probe in the direction which intersects at right angles with the insertion axis direction, a sector scanning type designed to obtain ultrasonic tomograms in the anterior direction by scanning the probe in, for example, the anterior direction which is parallel to the insertion axis direction, and other types.

For example, in U.S. Pat. No. 4,466,444 and Japanese Unexamined Patent Publication No. 7-289549, ultrasonic diagnostic devices which have structures where an ultrasonic search unit is provided at the tip part of an endoscope and upon rotation of this ultrasonic search unit, ultrasonic images of the section perpendicular to the insertion direction of the endoscope are obtained.

Moreover, Japanese Unexamined Patent Publication No. 62-176436 discloses an external type of ultrasonic search unit which obtains ultrasonic images of planes parallel to the insertion direction by directly rotating the ultrasonic search unit. In addition, Japanese Unexamined Patent Publication No. 62-231630 and Japanese Unexamined Patent Publication No. 1-136638 disclose ultrasonic search units having structures analogous to those of the above-mentioned Japanese Unexamined Patent Publication No. 62-176436.

Moreover, Japanese Unexamined Patent Publication No. 4-82540 discloses an ultrasonic probe in which two ultrasonic search units are provided at the tip of an insertion part and wherein these two ultrasonic search units are designed to scan in the direction vertical to the insertion direction and in the insertion axis direction, respectively.

Also, Japanese Unexamined Patent Publication No. 5-23337 discloses an endoscope in which an ultrasonic probe is inserted into a treatment device insertion hole such as a forceps channel or the like, and which has a protruding part with a tilted face located at the side of the opening direction of the forceps channel at the tip of the endoscope, a reflection plate provided on the tilted face, and a step part to fix the ultrasonic probe provided in the inside of the forceps channel, wherein the ultrasonic scanning direction can be changed and the diameter of the endoscope can be made small in size.

With the ultrasonic diagnostic device as set forth in the above-mentioned Japanese Unexamined Patent Publication No. 7-289549, however, ultrasonic images of a section vertical to the insertion direction of an endoscope can be obtained. Therefore, only one single cross section of a treatment device extended through a treatment device passage channel of the endoscope towards a diagnostic area is designated with almost punctiform lines on the ultrasonic images. Accordingly, it is inconvenient that the position of the tip of the treatment device can not be judged in the ultrasonic images.

As shown in FIG. 1, an ultrasonic search unit which is set forth in the above-mentioned Japanese Unexamined Patent Publication No. 1-136638 has a structure where an intermediate axis 104 is rotated by driving a motor 101 through spiral gears 102 and 103, and a pedestal 108 and a transducer 109 are rotated by rotation of the intermediate axis 104 through the first pulley 105, a belt 106, and the second pulley 107. In this device, the complicated structure makes the size of the tip part large.

Moreover, the ultrasonic probe of the above-mentioned Japanese Unexamined Patent Publication No. 4-82540 is disadvantageous in that the length of the hard body of the tip part becomes long due to the providing of two kinds of ultrasonic search units which differ in their scanning directions.

In addition, with the endoscope of Japanese Unexamined Patent Publication No. 5-23337, several problems have been encountered.

The first problem is that, although an ultrasonic probe is fixed by providing a step part, this fixing method may cause degeneration of ultrasonic images due to failure of steadily keeping a relative location between an ultrasonic search unit within the ultrasonic probe and a reflection plate provided in the endoscope.

The next problem is that, although the anterior scanning can be conducted by reflecting the ultrasonic waves emitted from the ultrasonic probe at the reflection plate provided in the endoscope to perform this scanning, it is required that an ultrasonic wave transmission medium be provided between the ultrasonic probe and the reflection plate. However, no structure is provided for this purpose.

Further, to insert the ultrasonic probe into a channel of the endoscope, and to conduct treatments under ultrasonic observation, two channels for treatment use must be provided in the endoscope. The problem is that, as a result, the overall diameter of the endoscope becomes large.

SUMMARY OF THE INVENTION

Accordingly, it is an object of the present invention to provide an ultrasonic diagnostic device where ultrasonic images do not suffer from degeneration.

It is another object of the present invention to provide an ultrasonic diagnostic device by which the position of the tip part of a treatment device can be confirmed under ultrasonic observation.

It is a further object of the present invention to provide an ultrasonic diagnostic device which is small and has a simple structure.

In short, an ultrasonic diagnostic device of the present invention which forms two scanning planes is composed of an ultrasonic search unit provided at the tip part of a long insertion part which conducts radial scanning by emitting ultrasonic waves in a direction vertical to the longitudinal axis direction of the insertion part, a reflector provided with the above-mentioned ultrasonic search unit which reflects a part of the ultrasonic waves emitted from the above-mentioned ultrasonic search unit to the anterior direction of the insertion part in order to scan the anterior direction of the insertion part, and a tip cap which covers the above-mentioned ultrasonic search unit and the above-mentioned reflector and which is made of a material which is permeable by the ultrasonic waves emitted from the above-mentioned ultrasonic search unit. Moreover, the ultrasonic endoscope which forms two scanning planes possesses a protruding part at the tip of the long insertion part and has a hemispherical part made of a material which is permeable by ultrasonic waves, an ultrasonic search unit provided within the protruding part which conducts radial scanning by emitting ultrasonic waves in a direction vertical to the longitudinal axis direction of the insertion part, a reflector provided with the above-mentioned ultrasonic search unit which reflects a part of the ultrasonic waves emitted from the above-mentioned ultrasonic search unit to the anterior direction of the insertion part in order to scan the anterior direction of the insertion part, and an optical system for observation which is located on the posterior plane of the above-mentioned protruding part.

BRIEF DESCRIPTION OF THE DRAWINGS

FIG. 2 to FIG. 16 are drawings to illustrate the embodiments of the present invention.

FIG. 2 is a drawing to show the schematic composition of an ultrasonic endoscope system.

FIG. 3 includes drawings to illustrate a structure of the tip part of an ultrasonic endoscope;

FIG. 3A is a drawing to show the tip part of an ultrasonic endoscope, including a partial cross section;

FIG. 3B is a cross section to illustrate the main part of FIG. 3A;

FIG. 3C is a 3C—3C cross section shown in FIG. 3B; and

FIG. 3D is a 3D—3D cross section shown in FIG. 3B.

FIG. 4 includes drawings to illustrate the structure of an ultrasonic search unit;

FIG. 5 is a drawing to illustrate a structure of the proximal ends of an ultrasonic wave transmission medium aspiration tube and an ultrasonic wave transmission medium injection tube.

FIG. 6 is a drawing to illustrate a lubricating oil hole which communicates with a guide tube.

FIG. 7 includes drawings to show the scanning conditions of an ultrasonic search unit;

FIG. 8 is a perspective view to show the scanning conditions of the ultrasonic search unit.

FIG. 9 is a diagram to show one example of an ultrasonic tomogram obtained with the ultrasonic search unit and displayed on a monitor screen.

FIG. 10 is a diagram where a balloon in the form of a bag is fitted at the tip cap.

FIG. 11 includes drawings to illustrate a balloon in the form of a tube which is designed to fit onto the tip cap;

FIG. 12 is a diagram to show a structure of the tip cap onto which a tube-shaped balloon is fitted.

FIG. 13 is a diagram to show a condition in which a tube-shaped balloon is fitted onto the tip cap.

FIG. 14 is a diagram to illustrate an operation to prevent rupture of the balloon.

FIG. 15 is a diagram to show a condition in which an ultrasonic endoscope is inserted into the bronchi to conduct treatment.

FIG. 16 includes drawings to illustrate an ultrasonic endoscope which is inserted into the bronchi to conduct treatments;

FIG. 17 includes drawings to illustrate an ultrasonic endoscope having an ultrasonic search unit of an electronic scanning type.

DESCRIPTION OF THE PREFERRED EMBODIMENT

Embodiments of the present invention will be described with reference to FIGS. 2 through 12.

Figure 1:
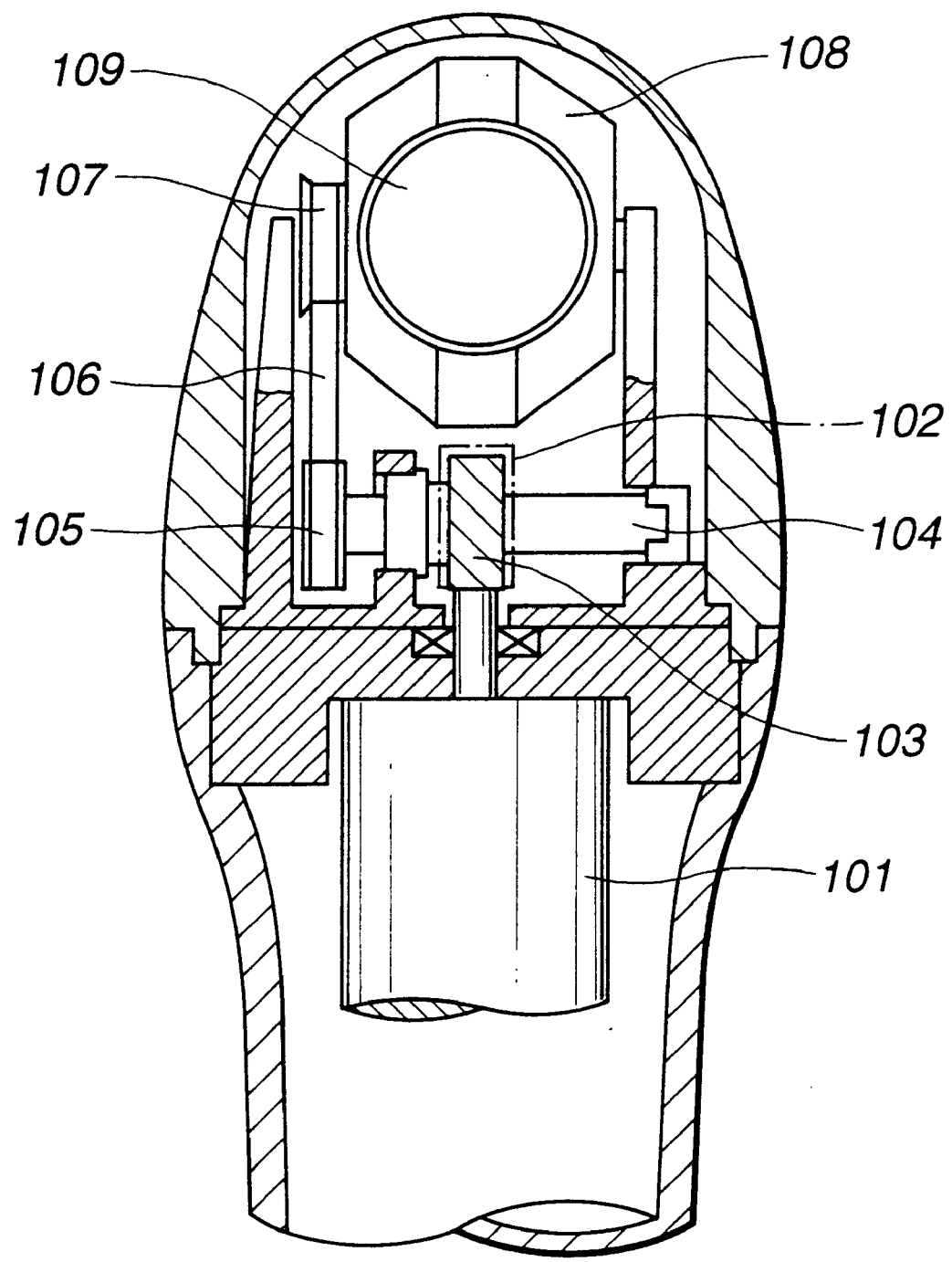
FIG. 1 is a drawing to show a structure of a conventional example.
Figure 2:
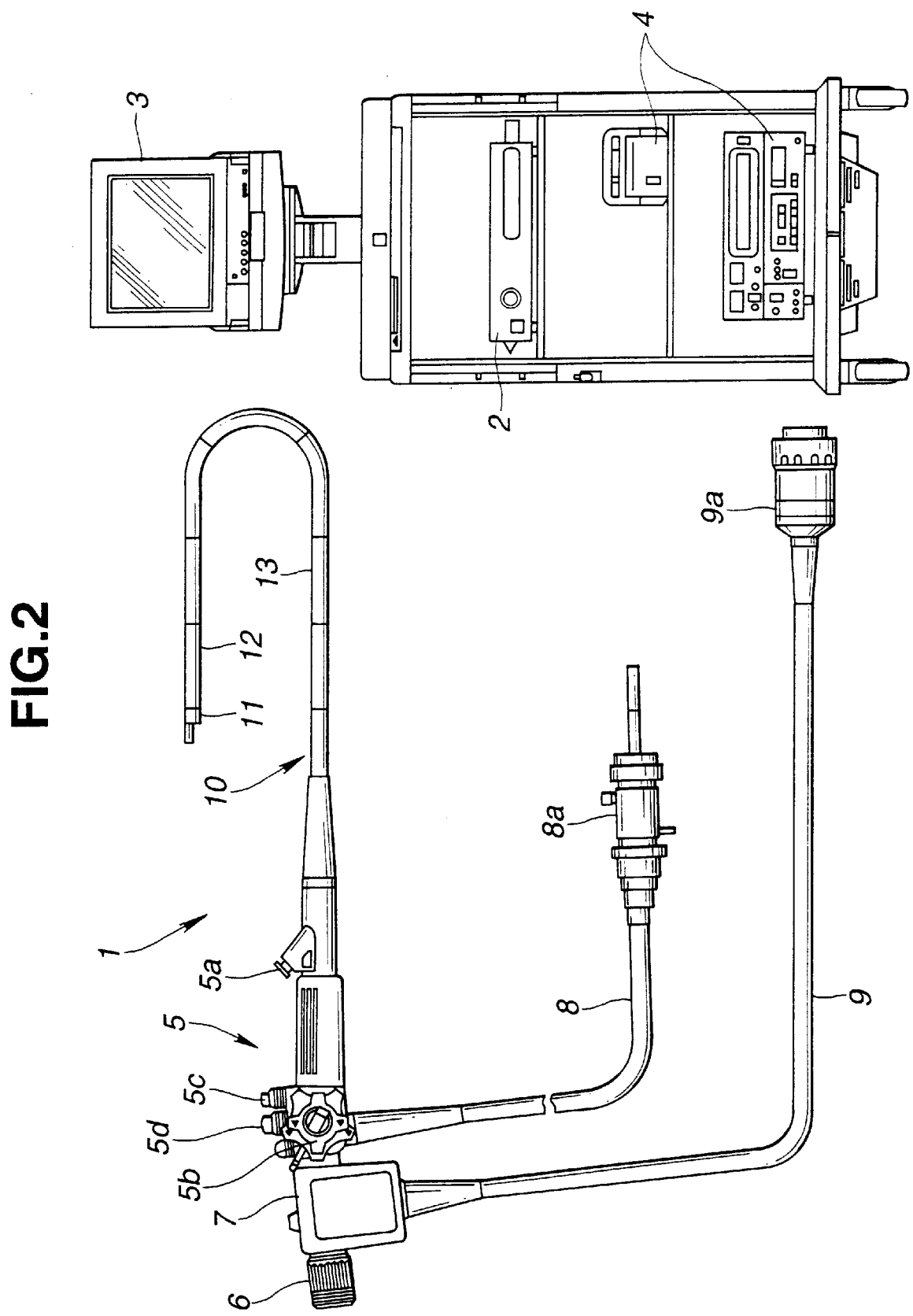

As shown in FIG. 2, an ultrasonic endoscope system of this embodiment is mainly composed of an ultrasonic endoscope (which is abbreviated as an endoscope hereinafter) 1 where an ultrasonic search unit is provided as an ultrasonic diagnostic device at an ultrasonic wave send/receive part protruding from an hard tip part 11 of an insertion part 10 to be described hereinafter, an ultrasonic observation device 2 including a signal conditioning part and the like for conditioning electric signals transferred from a light source (not shown in the figure) to illuminate an illuminating optical system and from the ultrasonic search unit, both of which are provided within endoscope 1, into image signals, a monitor 3 which is a display device to display image signals generated at ultrasonic observation device 2, and an image recording device 4 which includes a video device and a video printer to record the images designated on this monitor 3.

The ultrasonic endoscope 1 is mainly composed of the insertion part 10 which is inserted into a body cavity and is flexible, a main operation part 5 which is connected to the proximal end of this insertion part 10 and which serves also as a grip part, a sub-operation part 7 which includes an eyepiece part 6 at the back end and in which contains a rotary driving source such as a servomotor (not shown in the figure) or the like arranged inside, an optical cable 8 extending out from the lateral surface of the main operation part 5 and which includes a connector for light source 8a connected to a light source part (not shown in the figure) in a removable manner, and an ultrasonic cord 9 which extends out from the lateral surface of the sub-operation part 7 and includes at the proximal end part a connector for ultrasonic wave 9a which is removably connected to the signal conditioning part of the ultrasonic observation device 2.

The insertion part 10 is composed of, in their connected order from the tip, a hard tip part 11 which is made of a hard member, a bending part 12 which can be freely bent in the vertical and horizontal directions, and a flexible tube part 13 which is made of a slender, soft sheath.

At the main operation part 5, a treatment device insertion port 5a is provided to introduce a treatment device such as a puncture needle into a channel for treatment device passage 14 arranged within the insertion part 10 and shown in FIG. 3B. Moreover, in the main operation part 5, a bending operation knob 5b for bending operation of the bending part 12 in a desired direction, an air supply/water conveyance button 5c to provide air-supply and water-conveyance, an aspiration button 5d to conduct aspiration, and the like are provided.

As shown in FIG. 3B, the exit of the channel for treatment device passage 14 is an opening of the tip plane 11a of the hard tip part 11 which functions as a treatment device delivery port (described as a delivery port hereinafter) 14a.

As shown in FIG. 3A, a tip cap 20 is arranged at the side of the tip plane 11a of the hard tip part 11. Tip cap 20 is made of a plastic material such as a high-density polyethylene, polymethylpentene or the like which is superior in penetrability by ultrasonic waves, or is made of, for example, an elastic body which is permeable to ultrasonic waves.

Inside of this tip cap 20, an ultrasonic search unit 21 is provided to conduct radial scanning by emitting ultrasonic waves to the direction vertical to the longitudinal axis direction of the insertion part while being rotated in the a direction shown with the arrow "a" by means of, for example, a flexible shaft which will be described hereinafter. In addition, along with the ultrasonic search unit 21, a reflector 22 which has a reflection plane 22a to reflect a part of the ultrasonic waves emitted in the direction vertical to the longitudinal axis direction of the insertion part towards the anterior direction of the insertion part as shown with the alternating long and short dash line is provided. The reflection plane 22a of the reflector 22 is formed to be tilted at an angle of 45 degrees with respect to the ultrasonic search unit 21. An ultrasonic wave send/receive part 23 is composed of the ultrasonic search unit 21 and reflector 22.

The tip cap 20 is filled with an ultrasonic wave transmission medium such as a liquid paraffin, water, a liquid solution of carboxymethyl cellulose, a jelly or the like which is characterized by transmitting ultrasonic waves.

Furthermore, a groove 24 is provided for fitting a balloon which is filled with an ultrasonic wave transmission medium such as deaerated water or the like between the ultrasonic wave send/receive part 23 and a tissue to be treated or diagnosed. Moreover, a medium injection/aspiration part 25 is formed as a conduit opening to inject/aspirate an ultrasonic wave transmission medium such as deaerated water or the like to or from the inside of the balloon, and a water-conveyance/air supply groove 26 communicates with the medium injection/aspiration port 25. Therefore, the medium injection/aspiration port 25 has an opening on the bottom face of the water-conveyance/air supply groove.

As shown in FIGS. 3B, 3C and 3D, the insertion part 10 includes a channel for treatment device passage 14 to aspirate body fluids and to introduce a treatment device into a body cavity, a light guide 15 which is an illumination optical system to illuminate the inside of the body cavity, an image guide 16 which is an observation optical system in order to conduct observation of the inside of the body cavity, a flexible shaft 28 covered with a guide tube 27 and provided to rotate the ultrasonic search unit 21, a balloon water-conveyance/aspiration tube 29 which communicates with the medium injection/aspiration port 25, a medium injection tube 30 to inject an ultrasonic wave transmission medium into the above-mentioned tip cap 20, a medium aspiration tube 31 to aspirate the medium, and the like.

As shown in FIG. 3C, provided on the tip plane 11a of the above-mentioned hard tip part 11 are an optical system where a light guide 15 is arranged around an image guide 16, and the delivery port 14a of the channel for treatment device passage 14.

Under this situation, a plane which is formed by shifting a straight line which intersects the center of the delivery port 14a and the almost middle point of the reflection plane 22a of the reflector 22 in a direction towards the longitudinal axis of the insertion part is included within the scanning plane of the ultrasonic waves emitted from the ultrasonic search unit 21 in the anterior direction of the insertion part towards the direction vertical to the longitudinal axis direction of the insertion part and then reflected at the reflection plane 22a. In other words, it is ensured that a treatment device protruding from the delivery port 14a is within the scanning plane in the anterior direction of the insertion part when the ultrasonic waves are reflected at the reflection plane 22a.

Furthermore, light guide 15 is arranged to cover the circumference of the image guide 16. In addition, the guide tube 27 if filled with a lubricating oil. With this feature, the sliding property between the flexible shaft 28 and the inner circumference plane of the guide tube 27 is improved.

Figure 4A:
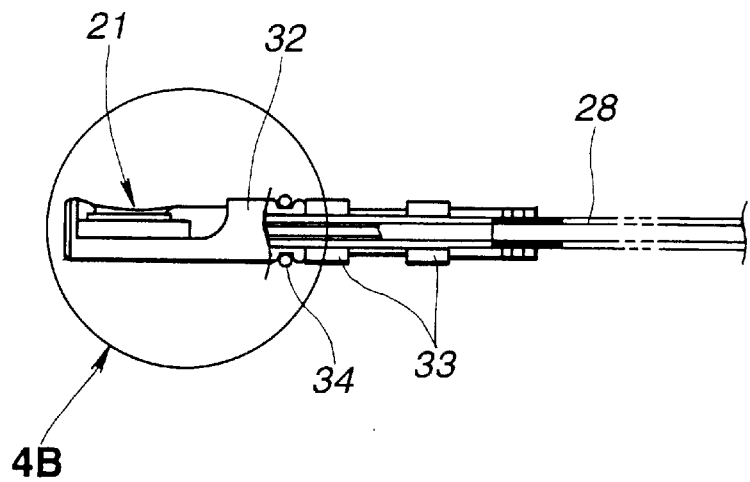
FIG. 4A is a drawing to show the structure of an ultrasonic search unit.

As shown in FIG. 4A, the ultrasonic search unit 21 is composed of the flexible shaft 28 which is extended out from a rotary driving source arranged in the operation part 7 and which is rotatable, a housing 32 which is fixed with the tip part of this flexible shaft 28 as one united body, a bearing part 33 which holds housing 32 to make it smoothly rotate by the torque of the flexible shaft 28, an O-ring 34 which ensures watertightness in the tip cap 20 and in the guide tube 27.

Figure 4B:
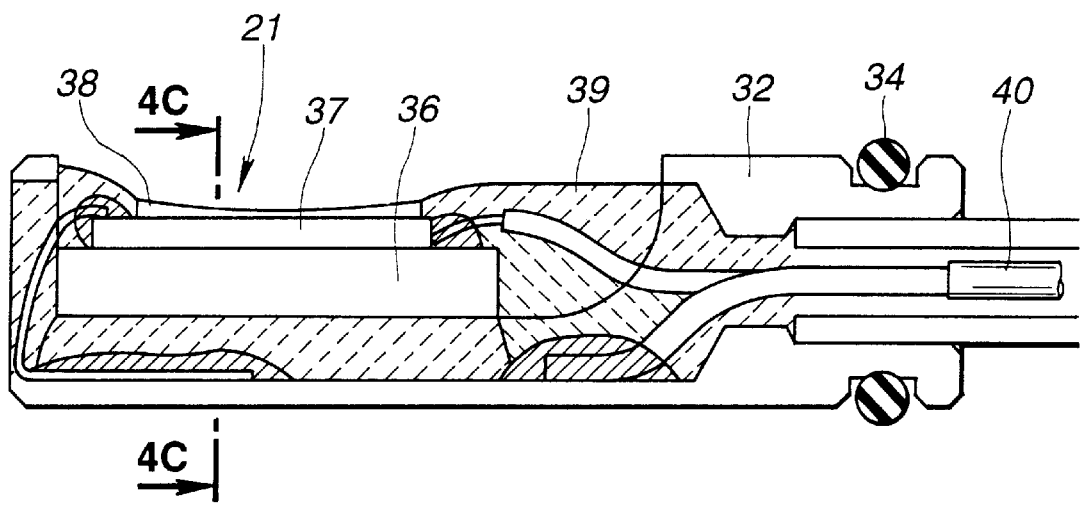
FIG. 4B is an enlarged section of the area labeled as 4B in FIG. 4A.
Figure 4C:
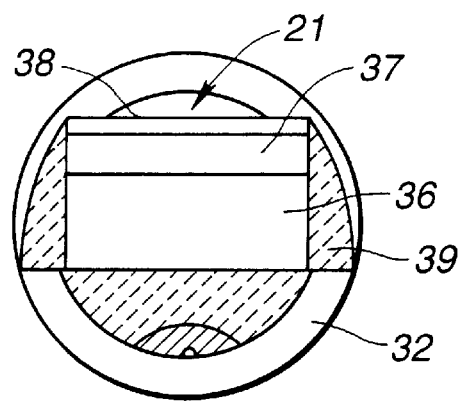
FIG. 4C is a 4C—4C cross section shown in FIG. 4B.

As shown in FIGS. 4B and 4C, in the above-mentioned housing 32, a backing material 36 which is an ultrasonic wave absorber formed by an elastic body such as ferrite-containing polychloroprene elastomer, tungsten powder-containing epoxy resin or the like, a plate-like piezo-electric element 37 such as zirconate titanate, titanate or the like, and an ultrasonic search unit 21 composed of a concave acoustic lens 38 which is made of epoxy resin are fixed to the housing 32 with an adhesive 39.

Furthermore, a signal line 40 passes through the inside of the flexible shaft and electrically connects the ultrasonic search unit 21 and the ultrasonic observation device 2 and then transfers ultrasonic driving signals and electrical signals which are received at the ultrasonic wave search unit and then converted.

Figure 5:
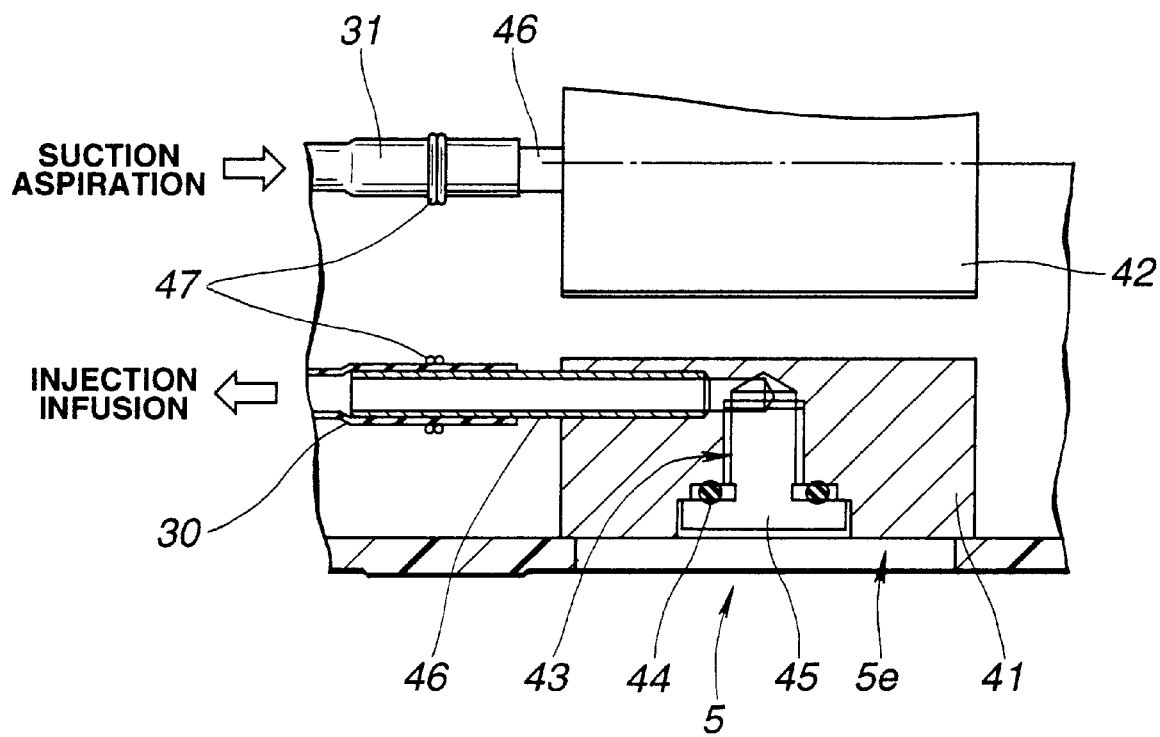

As shown in FIG. 5, the proximal end sides of the medium injection tube 30 and of the above-mentioned medium aspiration tube 31 are connected to a medium injection block 41 and a medium aspiration block 42, respectively, both of which are generally located on the inside of the insertion part 10 and are arranged within the grip part of the main operation part 5.

The medium injection block 41 and the medium aspiration block 42 have the same structure, where communication holes 43 which communicates with the medium injection tube 30 and medium aspiration tube 31, respectively, are formed. As shown in the figure, a seal screw 45 onto which an 0 ring 44 is arranged are screwed into the communication hole 43. When the seal screw 45 is taken out, injection and aspiration of an ultrasonic wave transmission medium into or from the tip cap 20 can be conducted.

In other words, when an ultrasonic wave transmission medium is to be injected into the above-mentioned tip cap 20, the medium is injected through the communication hole 43 of the medium injection block 41, while the medium is aspirated from tip cap 20 through communication hole 43 of the medium aspiration block 42.

The medium injection tube 30 and medium aspiration tube 31 are interfitted onto connection tubes 46 which are extended out from the medium injection block 41 and the medium aspiration block 42, respectively, and then are fixed as one united body by means of winding parts 47 which are provided on these interfitting parts. Moreover, at the position which corresponds to the communication hole 43 of the main operation part 5, a through hole 5e is formed to conduct desorption of the seal screw 45.

Figure 6:
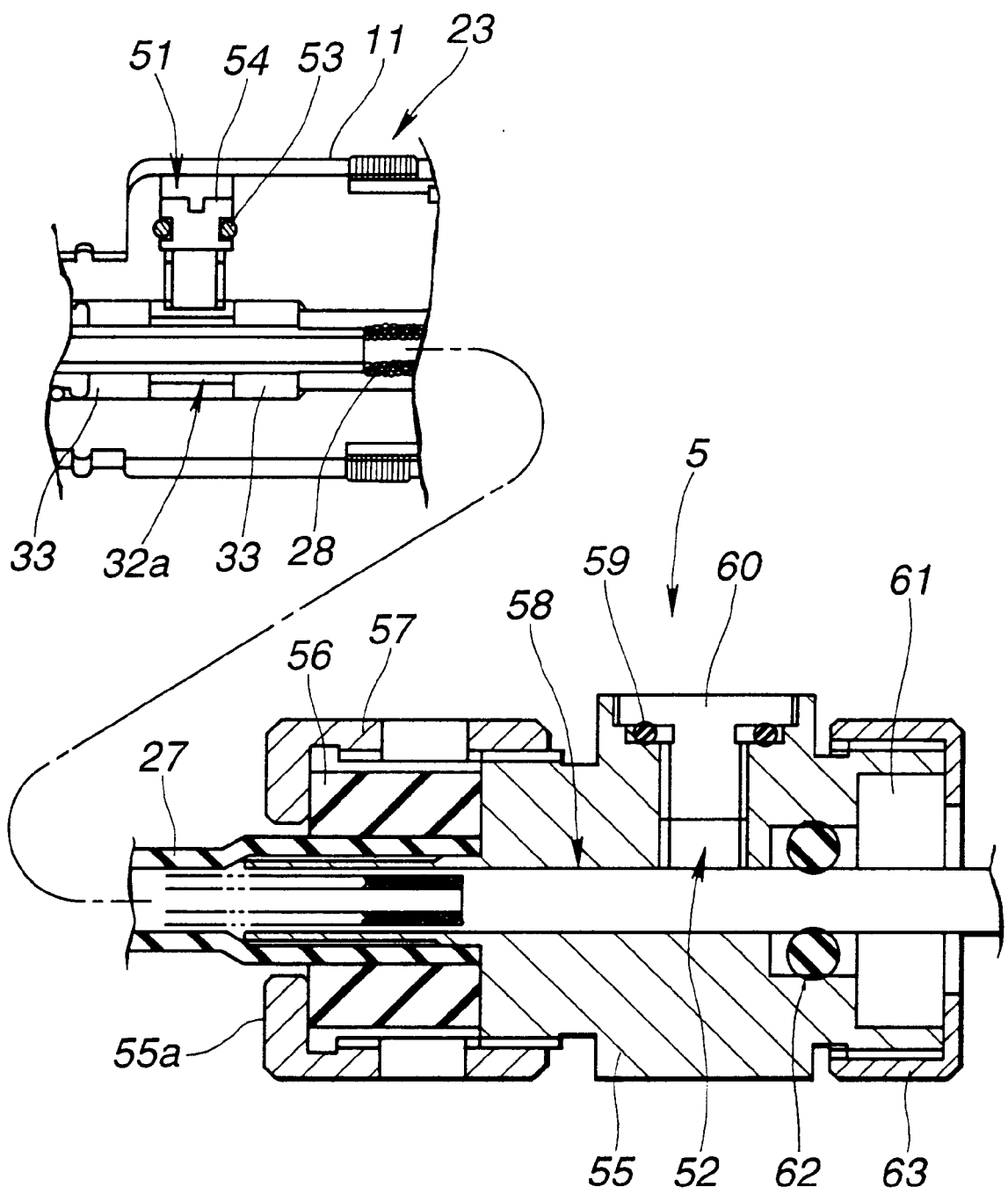

As shown in FIG. 6, at the hard tip part 11, the first lubricating oil hole 51 is formed between the two bearing parts 33 which are provided at the back side of the housing 32 of the ultrasonic search unit 21. First lubricating oil hole 51 communicates with a through hole 32a where a shaft affixed to the tip of the flexible shaft 28 passes.

Into this first lubricating oil hole 51, in almost the same manner as that of the communication hole 43, a seal screw 54 onto which an O ring 53 is arranged can be screwed.

On the other hand, the proximal end part of the guide tube 27 where the flexible shaft 28 is inserted is interfitted into a connection part 55a which protrudes from a block for lubricating oil 55 provided at the main operation part 5. And then, this guide tube 27 is designed such that by screwing a clamp screw member 57 where a clamping rubber 56 is provided into the block for lubricating oil 55, the clamping rubber 56 swells into the direction of its bore diameter and then secures this guide tube by a pushing pressure into the connection part 55a.

Moreover, in this block for lubricating oil 55, a shaft insertion hole 58 is formed through which the shaft affixed to the back end of the flexible shaft 28 passes. The second lubricating oil hole 52 communicates with this shaft insertion hole 58 at its middle part. Into this second lubricating oil hole 52, like the communication hole 43, a seal screw 60 onto which an O ring 59 is provided can be screwed.

In addition, under the condition where the seal screw 54 and seal screw 60 are both taken out, by injecting a lubricating oil from one of the lubricating oil holes 51 or 52 and by aspirating the lubricating oil from the other lubricating oil hole 52 or 51, the inside of the guide tube 27 can be filled with lubricating oil.

Furthermore, a bearing part 61 bears the shaft part connected to a coil shaft. A watertight ring 62 protects against outflow of lubricating oil through this shaft part. A cap screw member 63 which protects against dislodging of the above-mentioned bearing part 61.

The operations of the ultrasonic endoscope 1 having the structure described hereinbefore will be illustrated below.

An operator passes the insertion part 10 of the ultrasonic endoscope 1 towards an area of interest, while looking into the eyepiece part 6 to observe the body cavity. And then, when it is confirmed that the tip cap 20 which is arranged at the end of hard tip part 11 of the insertion part 10 reaches an area of interest, in order to conduct ultrasonic scanning, the operator drives the motor within the sub-operation part 7 while starting transmission of high voltage pulses from the ultrasonic observation device 2 to the ultrasonic search unit 21.

Then, as the flexible shaft 28 starts to rotate, by means of the high voltage pulses transmitted, the ultrasonic search unit 21 is excited to emit ultrasonic waves.

Figure 7A:
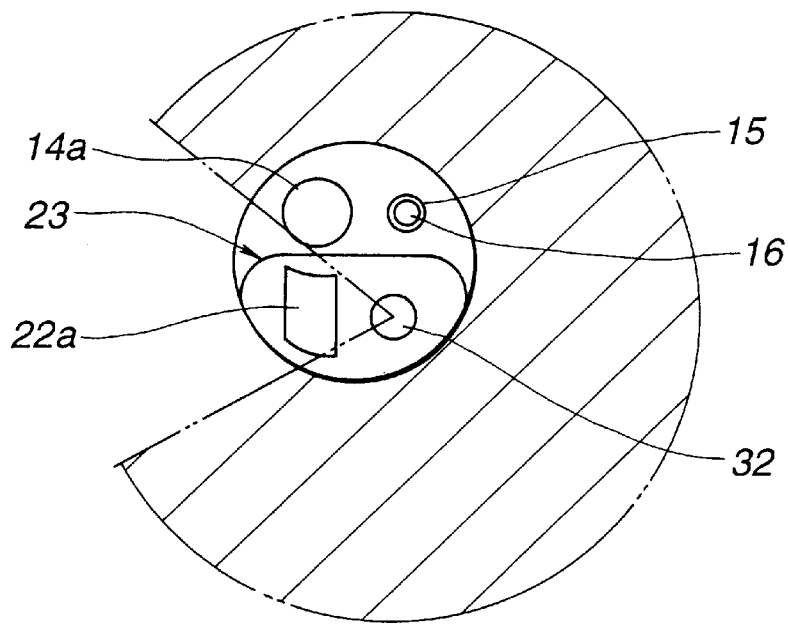
FIG. 7A is a drawing to show the scanning conditions when the ultrasonic endoscope is observed from the front.

The housing 32 rotates by means of the rotation of the flexible shaft 28, and the ultrasonic waves emitted from the ultrasonic search unit 21 in the direction vertical to the longitudinal axis direction of the insertion part travel through the tip cap 20 and then spread to a biological tissue as shown in the area filled with slanted lines in FIG. 7A in this manner, radial scanning is effected in areas where ultrasonic waves are emitted in the direction vertical to the longitudinal axis direction of the insertion part.

Figure 7B:
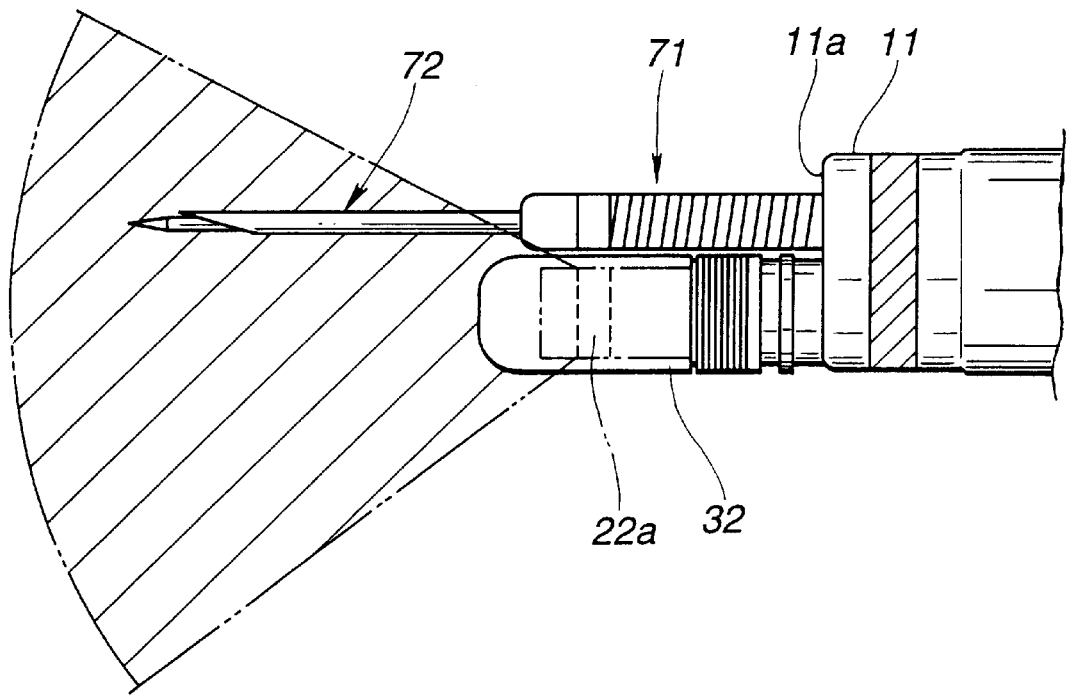
FIG. 7B is a drawing to show the scanning conditions when the ultrasonic endoscope is observed from the side.

Then, when the ultrasonic waves emitted from the ultrasonic search unit 21 cover onto the reflection plane 22a, as shown in FIG. 7B, the ultrasonic waves are reflected off of reflection plane 22a to thereby scan the anterior direction of the insertion part as shown in the area filled with the slanted lines.

Moreover, when the housing 32 rotates and the ultrasonic waves emitted from the ultrasonic search unit 21 travel through the reflection plane 22 again, as shown in FIG. 7A, the ultrasonic waves emitted from the above-mentioned ultrasonic search unit 21 travel through the tip cap 20, spread in the direction vertical to the longitudinal axis direction of the insertion part, and scan the plane which is vertical to the longitudinal axis direction of the insertion part and which is shown with the slanted lines.

Figure 8:
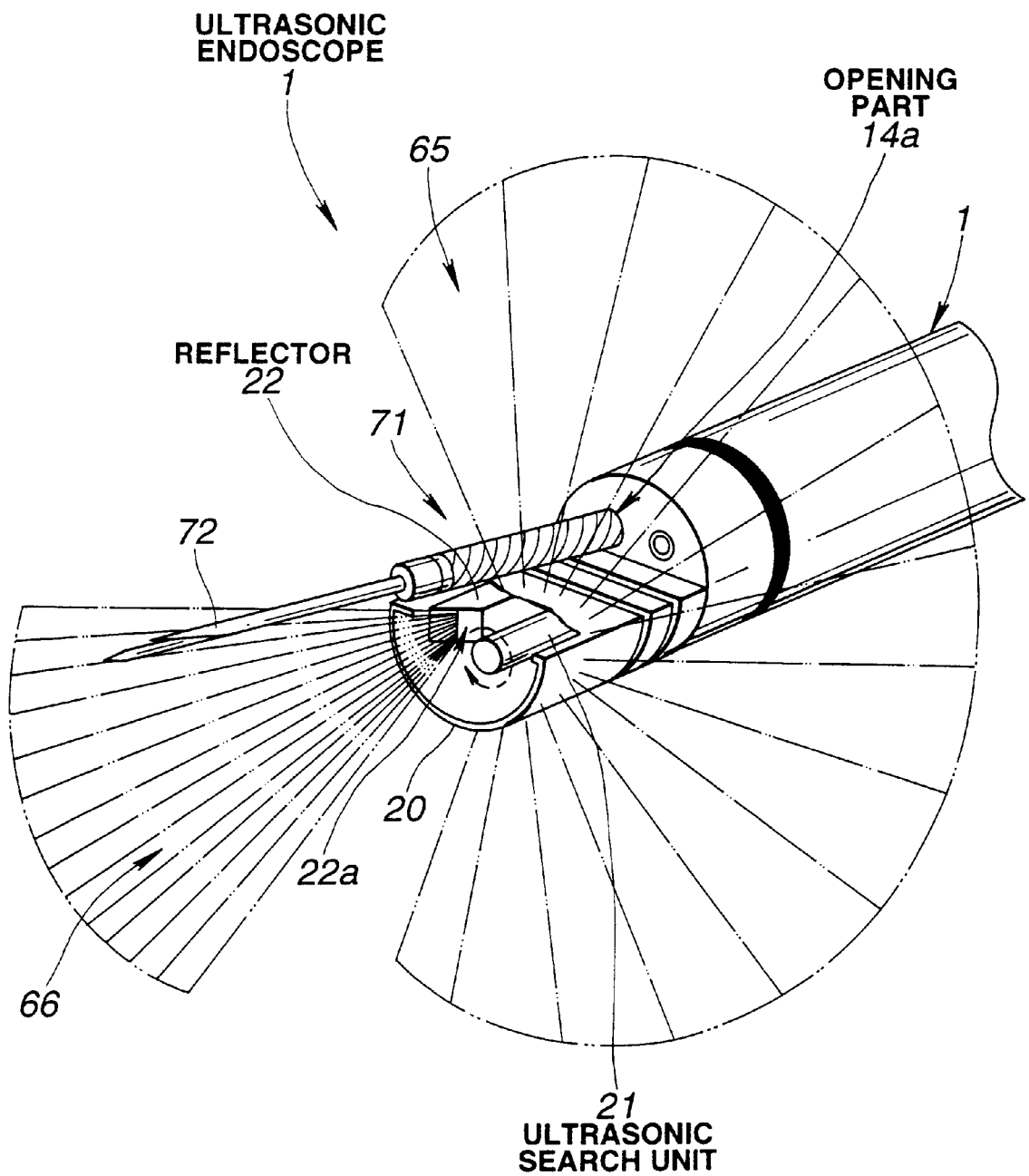

In short, as shown in FIG. 8, the ultrasonic endoscope 1 of this embodiment has the ultrasonic search unit 21 which rotates by means of the flexible shaft 28, and the reflector 22 provided along with the housing 32 of this ultrasonic search unit 21 and which forms the reflection plane 22a, both within the tip cap 20. In this manner, one single rotatable ultrasonic search unit 21 has two scanning areas, namely, the radial scanning area 65 where the ultrasonic waves are emitted in the direction vertical to the longitudinal axis direction of the insertion part and the scanning area in the anterior direction of the insertion part 66 in which the ultrasonic waves are emitted on the direction anterior to the longitudinal axis direction of the insertion part.

Figure 9:
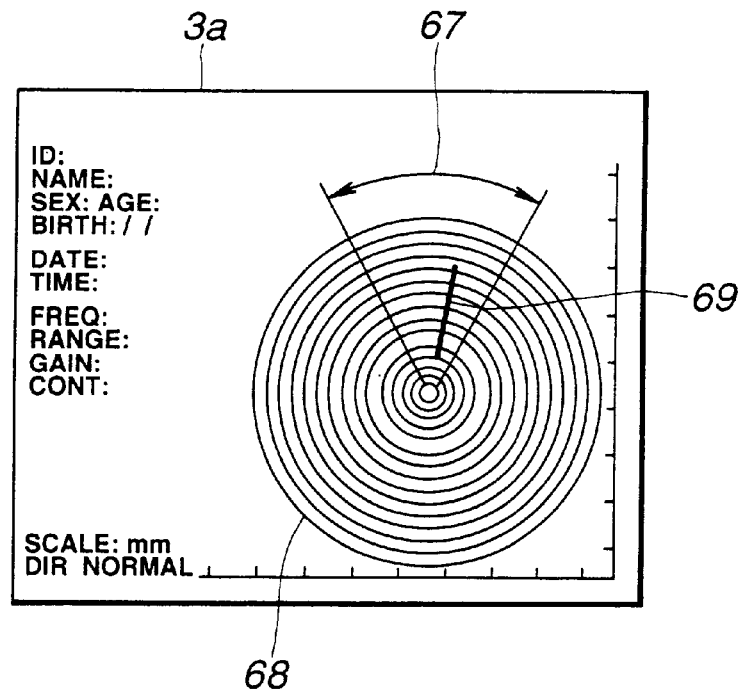

For this reason, as shown in FIG. 9, both a radial ultrasonic tomogram 68 which is obtained from radial scanning in a plane vertical to the longitudinal axis direction of the insertion part and an ultrasonic tomogram in the anterior direction of the insertion part 67 which is obtained from radial scanning in the plane in the anterior direction of the insertion part are displayed concentrically on the screen of the monitor 3.

As described hereinabove, under ultrasonic observation of these two scanning areas, by inserting a treatment device such as a tissue puncture needle (which is abbreviated as a puncture needle hereinafter) 71 or the like to extend puncture needle 71 from the delivery port 14a through the channel for treatment device passage 14 into a body cavity (see FIG. 7B and FIG. 8), puncture needle 71 can be readily moved towards an observation area.

Then, since the plane formed along the central axis of delivery port 14a and the almost center point of the reflection plane 22 and the scanning plane in the anterior direction of the insertion part almost coincide, the needle part 72 of the puncture needle 71 which protrudes from the delivery port 14a is arranged within the scanning area in the anterior direction of the insertion part, the scanning are being formed by the ultrasonic waves reflected at the above-mentioned reflection plane 22a.

In this manner and as shown in FIG. 9, within the ultrasonic tomogram in the anterior direction of the insertion part 67 which represents the above-mentioned scanning area 66 in the anterior direction of the insertion part on the screen 3a of the monitor 3, an image of the needle part 69 up to the tip of the needle part 72 of the puncture needle 71 protruding from the delivery port 14a is depicted. Then, by means of the image of the needle part 69 displayed on screen 3a, suction of selected tissues can be conducted easily and safely while confirming the relative location of tip of the puncture needle 71 and the observation area, depth of the puncture, and the like.

In this manner, by providing within the tip cap, along with the housing, the reflector having the reflection plane to reflect a part of the ultrasonic waves emitted in the direction vertical to the longitudinal axis direction of the insertion part and from the ultrasonic search unit arranged at the tip part of the flexible shaft which is rotated by the driving source to the tip direction of the insertion part, both the radial scanning area which is vertical to the longitudinal axis direction of the insertion part and the scanning area in the anterior direction of the insertion part can be obtained without having to form the tip part with a wide diameter and further can be obtained with one single rotatable ultrasonic search unit.

In addition, since the central axis of the delivery port is provided so that the treatment device protruding from the channel for treatment device passage is arranged within the scanning area in the anterior direction of the insertion part, up to the tip of the treatment device protruding from the delivery port can be depicted on the ultrasonic tomogram.

Thus, when conducting puncture under ultrasonic observation, collection of tissues can be performed safely and swiftly while confirming not only the puncturing position of the puncture needle but also the depth of puncture.

In other words, the present invention solves the problem that when only ultrasonic images which are vertical to the inserting direction of an endoscope are displayed, only a single cross-section of the needle part of the puncture needle inserted to collect tissues is designated with almost punctiform lines, whereby the position of the needle tip can not be confirmed.

More, to conduct ultrasonic observation with intervention of an ultrasonic wave transmission medium between the ultrasonic search unit and an observation area, for example, a method generally called a filling method is used wherein water is injected into an observation area such as the stomach or the like to submerge both the observation area and the ultrasonic search unit of the ultrasonic endoscope. Similarly, a method generally known as a balloon sticking method can be used, wherein a balloon is fitted at the tip cap of the ultrasonic endoscope, an ultrasonic wave transmission medium is injected into this balloon, and then the swollen balloon is stuck onto the observation area.

Figure 10:
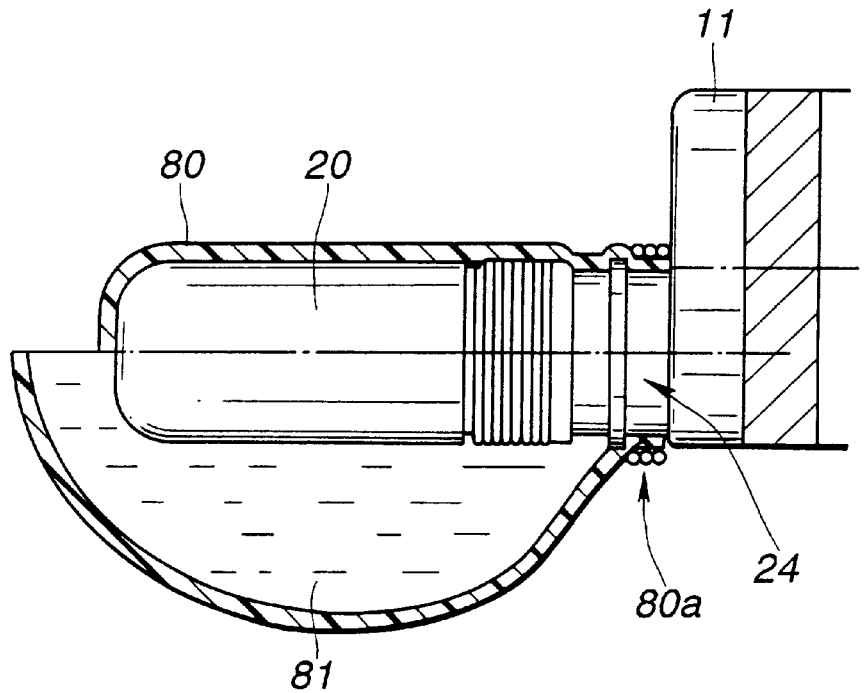

With the above-mentioned balloon sticking method, as shown in FIG. 10, to a groove for balloon fitting 24 is formed on the above-mentioned tip cap 20. The balloon 80 is fixed by means of, for example, a tying string 80a. Upon expanding this balloon 80 by injecting an ultrasonic wave transmission medium 81 into the inside of the balloon 80, this swollen balloon 80 contacts the observation area whereby ultrasonic images can be obtained. The balloon 80 can be made of an extensible member such as latex, Teflon, or the like which is retractable and has an ultrasonic permeability, and has an opening provided at one end thereof. Therefore, when an excessive amount of an ultrasonic wave transmission medium is injected into the balloon, the balloon swells too much in the anterior direction resulting in the possibility of failure to contact the observation area, and also of rupture of the balloon due to the excessive injection.

Figure 11A:
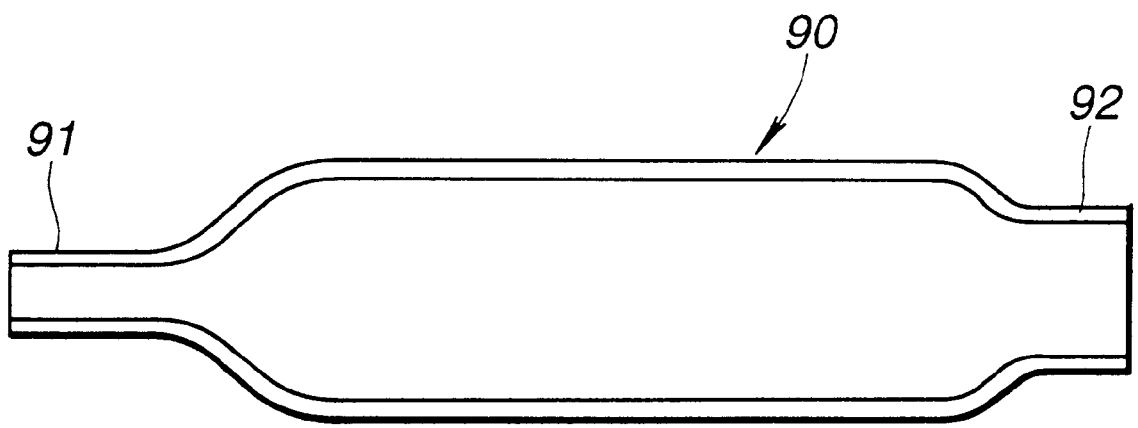
FIG. 11A is a diagram to show the balloon.
Figure 11B:
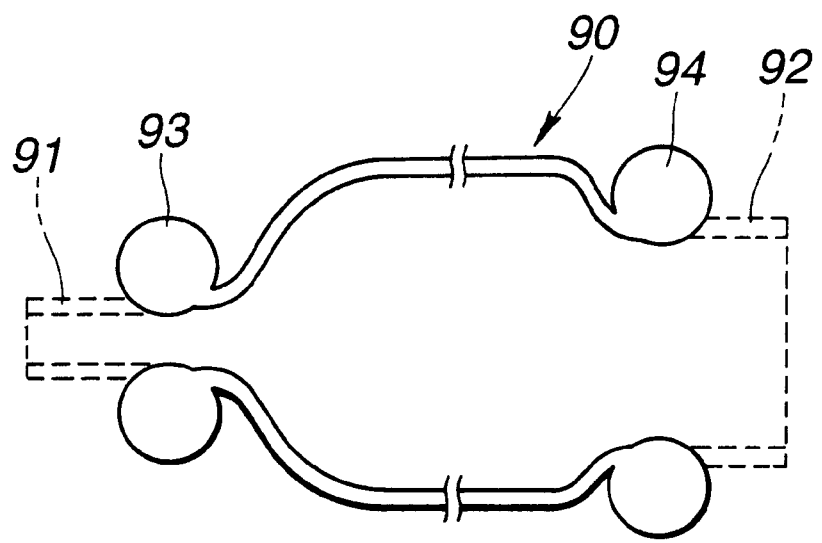
FIG. 11B is a diagram to illustrate fitting parts provided at both ends of the balloon.

Then, as shown in FIG. 11A, a balloon 90 arranged to cover almost the full circumferential surface of the tip cap 20 is formed almost as a tube with openings at both ends, and also with small diameter parts 91 and 92. Moreover, as shown in FIG. 11B, the balloon 90 has a design where the small diameter parts 91 and 92 which are shown with the broken lines at both ends of the balloon 90 can be successively rolled in toward the main portion of the balloon to form fitting parts 93 and 94 which have O ring functions, and then these fitting parts 93 and 94 can be fitted into the tip cap which is described hereinafter.

Figure 12:
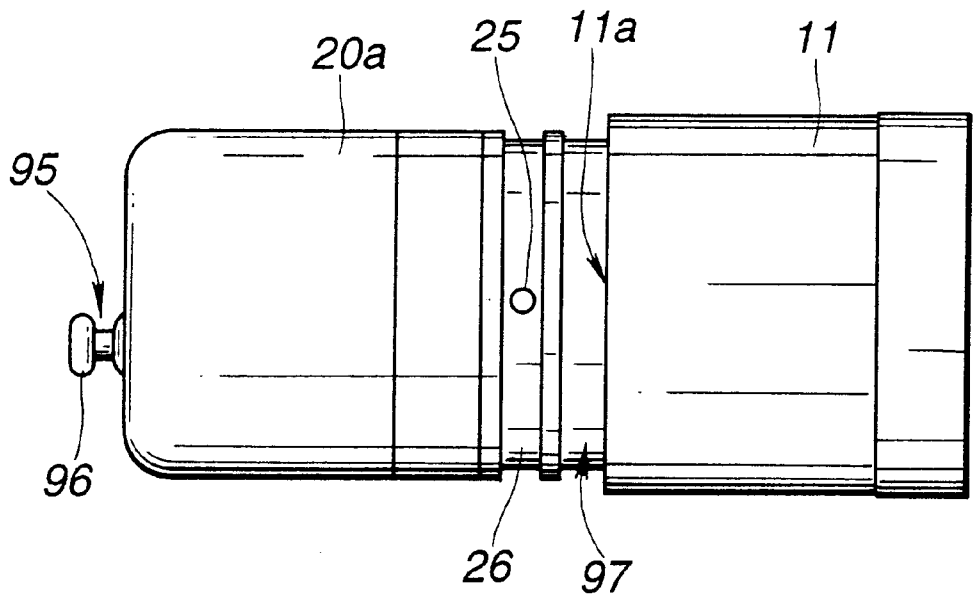

Furthermore, because the fitting parts 93 and 94 are formed at both ends of the balloon 90, as shown in FIG. 12, at the tip plane of the tip cap 20a, a convex part 96 is provided where a groove for balloon fitting at the tip side 95 is formed whereupon the above-mentioned fitting part 93 can be arranged. In addition, the above-mentioned fitting part 94 can be arranged onto a groove 97 for balloon fitting formed at the back end of tip cap 20, wherein groove 97 is the same as the groove for balloon fitting 24.

Figure 13:
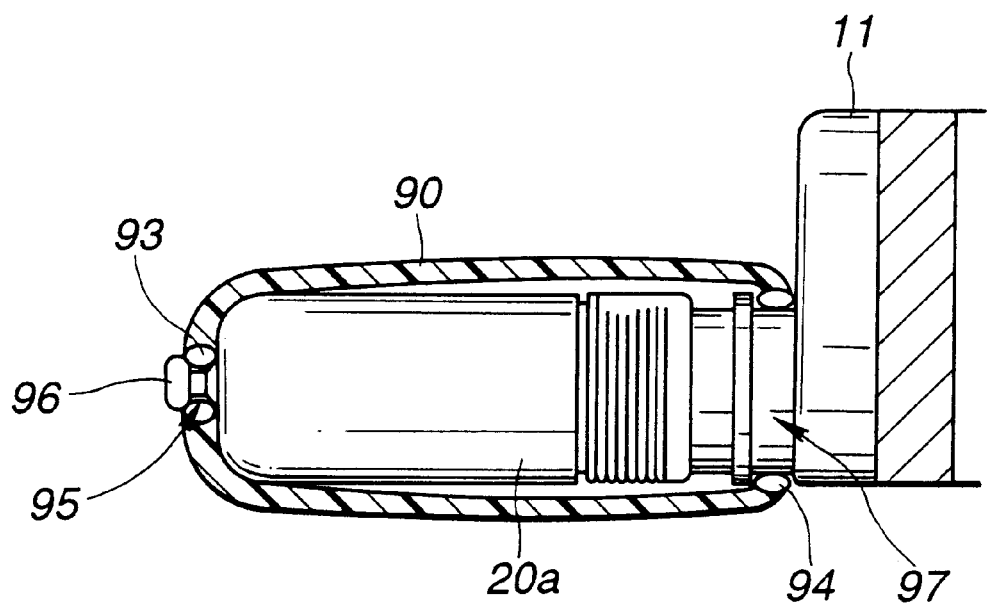

In other words, as shown in FIG. 13, after arranging the fitting part 94 onto the groove 97 for balloon fitting at the back end, the fitting part 93 is arranged onto the groove 95 for balloon fitting at the tip side. In this manner, the circumferential surface of the tip cap 20a is covered with the balloon 90.

In this situation, by injecting the ultrasonic wave transmission medium 81 into the balloon 90, the balloon 90 swells. If an amount of ultrasonic wave transmission medium 81 which is more than necessary is injected, the balloon 90 will expand too much and its internal pressure will increase, resulting in a force which presses the fitting part 93 towards the tip in the longitudinal direction.

Figure 14:
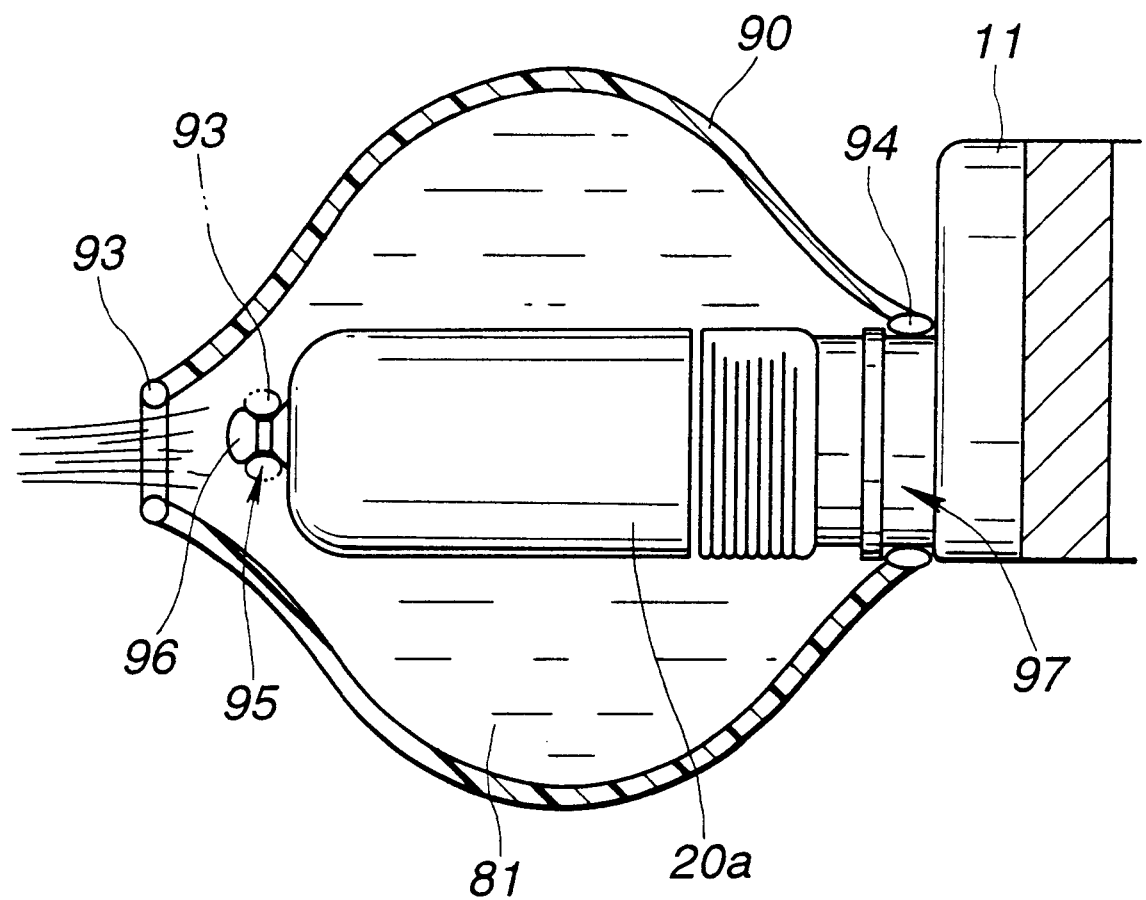

Then, before rupture of the balloon 90, by means of the pressing force of the fitting part 93 as shown in FIG. 14, the fitting part 93 is released from the groove 95 for balloon fitting at the tip. In this manner, the ultrasonic wave transmission medium 81 is drained into a body cavity from the opening of the small diameter part 91 of the balloon 90 upon disengagement from groove 95. Since the fitting part 94 is arranged onto the groove 97 for balloon fitting at the back end the balloon 90 never falls into the abdominal cavity.

In this manner, by designing the balloon in a tube form, when an excessive amount of an ultrasonic wave transmission medium is injected into the balloon, before rupture the fitting part is moved away from the groove for balloon fitting at the tip side and then the ultrasonic wave transmission medium injected in the balloon is drained to the outside so that rupture of the balloon due to a surplus supply of ultrasonic wave transmission medium can be prevented.

Moreover, even when an operator tries to pull off the ultrasonic probe compulsorily while the balloon is still swollen, since the inside pressure of the balloon increases due to the addition of the external pressure onto the balloon, the fitting part is moved away from the groove for balloon fitting at the tip so that the ultrasonic wave transmission medium injected into the balloon is drained to the outside, also in this case, so that rupture of the balloon can be prevented. Furthermore, since in either case, the fitting part at the proximal end of the balloon is arranged onto the groove for balloon fitting at the back end, the falling of the balloon into a body cavity is prevented.

Examples of use of the ultrasonic endoscope 1 will be illustrated with reference to FIG. 15 and FIG. 16 hereinafter.

The bronchi is an example of one area which can be treated using the ultrasonic endoscope 1. The inside of the bronchi is normally filled with air. Therefore, when ultrasonic diagnosis is conducted, the balloon 80 is fitted onto the groove for balloon fitting 24 in advance.

Figure 15:
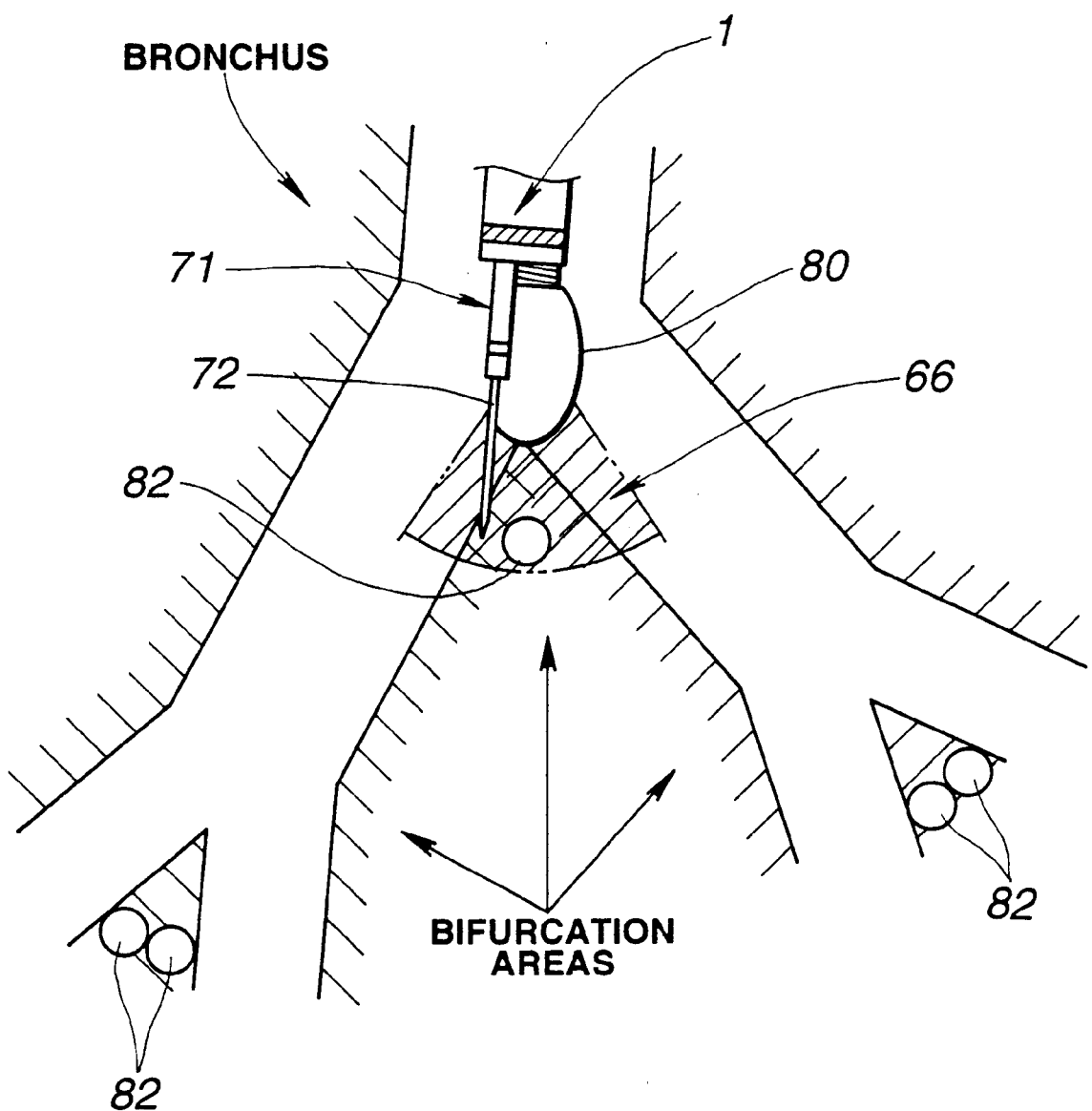

As shown in FIG. 15, the ultrasonic endoscope 1 is inserted into a bronchus, and then when the ultrasonic endoscope 1 reaches the area of interest for ultrasonic diagnosis, the puncture needle 71 is protruded onto the tip cap 20 to which the balloon 80 is fitted.

Figure 16A:
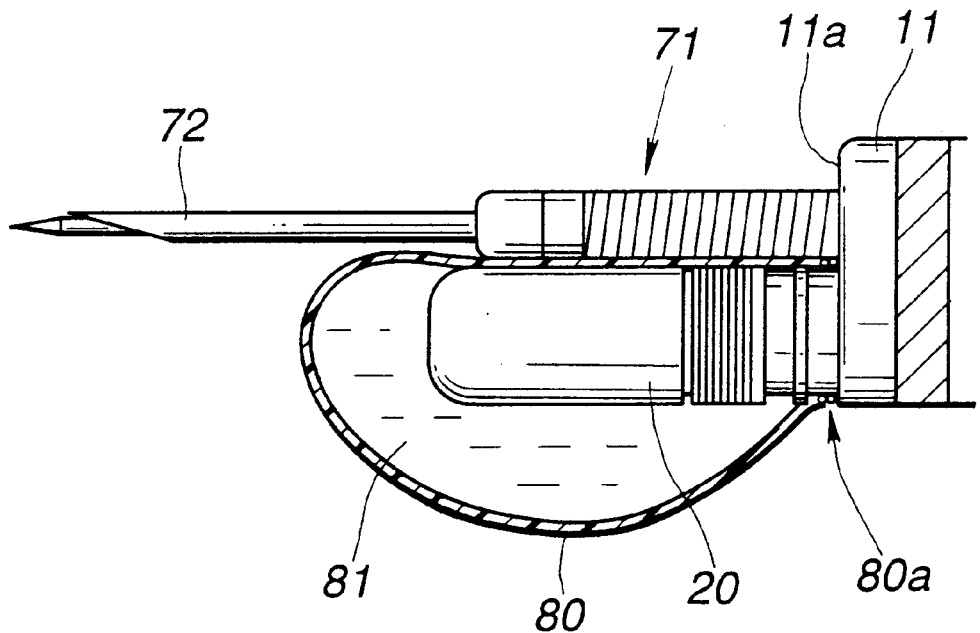
FIG. 16A is a drawing to show the relative location between a protruding puncture needle and a swollen balloon on an ultrasonic endoscope viewed from the side.
Figure 16B:
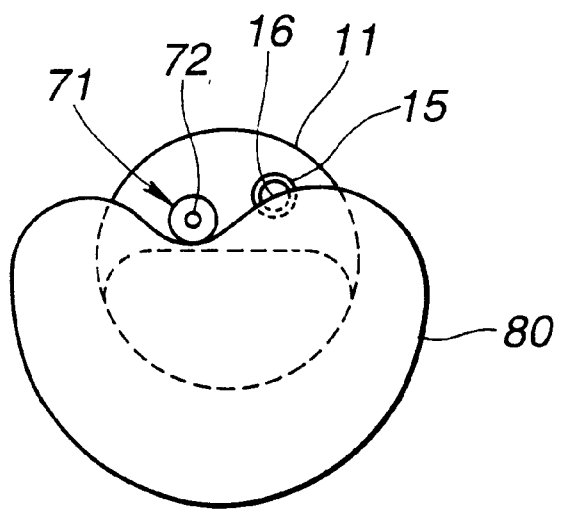
FIG. 16B is a drawing to show the relative location between a protruding puncture needle and a swollen balloon on an ultrasonic endoscope viewed from the front.

In this situation, the ultrasonic wave transmission medium 81 such as deaerated water or the like is injected into the balloon 80 to expand the balloon 80 as shown in FIG. 16A. At this time, a part of the balloon 80 which is swelling up as shown in FIG. 16B is expanding while being restricted by the puncture needle. Specifically, the balloon 80 is swelling around the puncture needle 71, wherein it swells in each direction which is not restricted, namely to the right and the left, as well as in the anterior and posterior directions. And when the balloon 80 which is filled with the ultrasonic wave transmission medium 81 is positioned between the area to be tested and the tip cap 20, ultrasonic diagnosis is enabled, whereupon ultrasonic scanning is started.

Then, since this ultrasonic endoscope 1 scans both the radial scanning area 65 and the scanning area in the anterior direction of the insertion part 66, the lymph node 82 is displayed within the ultrasonic tomogram in the anterior direction of the insertion part 67 which represents the scanning area in the anterior direction of the insertion part 66.

At this time, the puncture needle 71 is to be protruded. Then, under ultrasonic observation, the needle part 72 is depicted as an image 69 within the ultrasonic tomogram in the anterior direction of the insertion part 67. By puncturing into the lymph node 82 while confirming the image 69, collection of tissues can be conducted safely and securely.

In this manner, by using an ultrasonic endoscope which possesses both the radial scanning area and the scanning area in the anterior direction of the insertion part, confirmation of the existence or absence of metastasis of malignant neoplasm at bifurcation areas into the lymph node is securely conducted, which is essential to determine the procedure to be followed in, for example, the bronchi.

Figure 17A:
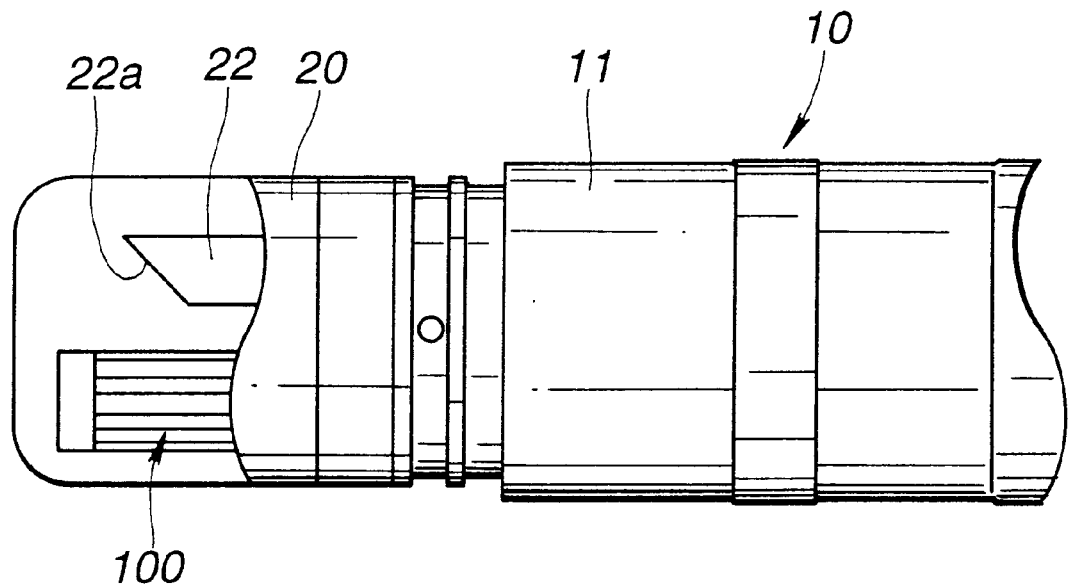
FIG. 17A is a drawing to show the tip part of the ultrasonic endoscope of the electronic scanning type, including a partial cross section.
Figure 17B:
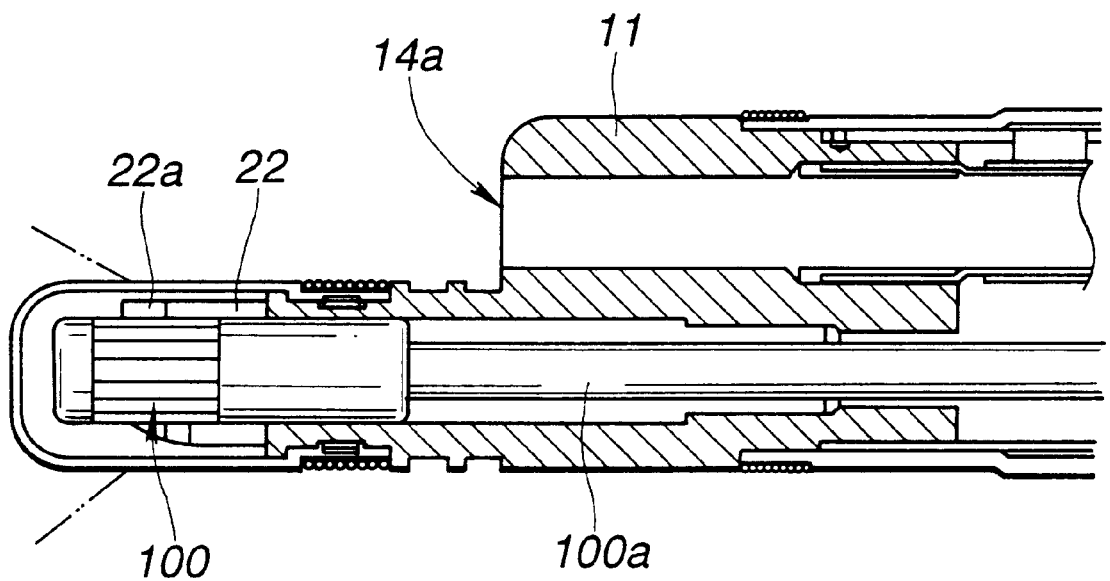
FIG. 17B is a cross sectional view to illustrate the main part of FIG. 17A.

Furthermore, although in this embodiment the ultrasonic search unit is illustrated as a mechanical radial scanner, the scanning method is not limited to mechanical radial scanning. In other words, instead of providing the ultrasonic search unit at the tip part of the flexible shaft, an electronic radial scanner may be used, such as that shown in FIG. 17A and FIG. 17B, wherein an ultrasonic search unit of an electronic scanner 100 and an oscillator cable 100*a* are provided.

In this manner, the same operations and advantages as those of the above-mentioned embodiment can be obtained. The operating capabilities of the ultrasonic endoscope can further be improved, because the flexible shaft provided in the above embodiment, the driving part which rotates this flexible shaft, and the sub-operation part where the driving part is provided are all no longer necessary. In addition, by connecting to an ultrasonic diagnostic device which allows color Doppler processing, color Doppler display can be enabled.

In the present invention, it is clear that a wide variety of embodiments can be formed based on the present invention without departing from the spirit and scope of the present invention. The present invention is not to be limited by any specific embodiments, but restricted only by the appended claims.

I claim:

1. An ultrasonic diagnostic device which forms two scanning planes, comprising:

a lone insertion part having a tip and a longitudinal axis;

an ultrasonic search unit provided at the tip of the insertion part and which conducts radial scanning by emitting ultrasonic waves in a direction vertical to the longitudinal axis of the insertion part;

a reflector provided at the tip of the insertion part and having a reflection plane which reflects a portion of the ultrasonic waves emitted from the ultrasonic search unit in a direction anterior to the insertion part in order to scan anteriorly of the insertion part; and a tip cap which covers the ultrasonic search unit and the reflector and which is made of a material that is permeable to the ultrasonic waves emitted from the ultrasonic search unit.

2. An ultrasonic diagnostic device according to claim 1, wherein the insertion part further includes a channel for treatment device passage through which treatment devices can be inserted, the channel having a delivery port formed at the tip of the insertion part so that a treatment device extended from said delivery port will be located within a scanning area in the anterior direction of the insertion part formed when ultrasonic waves are reflected at the reflector.

3. An ultrasonic diagnostic device according to claim 2, wherein the scanning area in the anterior direction of the insertion part is formed alone a plane defined by shifting a straight line which intersects the center of the delivery port and a point approximately at the center of the reflection plane in the direction of the longitudinal axis of the insertion part.

4. An ultrasonic diagnostic device according to claim 2, wherein the tip cap extends from the tip of the insertion part more distally than the delivery port.

5. An ultrasonic diagnostic device according to claim 4, wherein the inside of the tip cap is filled with an ultrasonic wave transmission medium which transmits ultrasonic waves.

6. An ultrasonic diagnostic device according to claim 4, further comprising a balloon removably attached to the tip cap, wherein the balloon is expandable upon being filled with an ultrasonic wave transmission medium.

7. An ultrasonic diagnostic device according to claim 6, wherein the balloon has a bag shape with an opening at one end thereof.

8. An ultrasonic diagnostic device according to claim 6, wherein the balloon has a tube shape with openings at both ends thereof.

9. An ultrasonic diagnostic device according to claim 7, wherein the tip cap includes a groove formed at the proximal end of the tip cap, the opening of the balloon being attached to the tip cap at the groove.

10. An ultrasonic diagnostic device according to claim 8, wherein the tip cap includes a groove formed at each of the distal end and the proximal end respectively, of the tip cap, the opening of the balloon being attached to the tip cap at the grooves.

11. An ultrasonic diagnostic device according to claim 6, wherein when the balloon is fitted onto the tip cap and is in an expanded state, the tip cap is positioned within the balloon and a treatment device inserted through the channel and extended from the delivery port is positioned along an exterior surface of the balloon.

12. An ultrasonic diagnostic device according to claim 1, wherein the ultrasonic search unit is one of a mechanical scanner or an electronic scanner.

13. An ultrasonic diagnostic device according to claim 2, further including a display device to synthesize radial ultrasonic tomograms obtained by the radial scanning of the ultrasonic search unit and ultrasonic tomograms obtained by scanning in the anterior direction of the insertion part with the ultrasonic waves reflected anteriorly by the reflector, and then to successively display the resulting images.

14. An ultrasonic diagnostic device according to claim 13, wherein the images to be displayed on the display device are circular.

15. An ultrasonic endoscope which forms two scanning planes, comprising:

a long insertion part having a tip and a longitudinal axis;

a protruding portion provided at the tip of the insertion part and which has a semicylindrical share, and is made of a material which is permeable to the ultrasonic waves;

an ultrasonic search unit provided within the protruding part and which conducts radial scanning by emitting ultrasonic waves in a direction vertical to the longitudinal axis of the insertion part;

a reflector provided within the protruding part and having a reflector plane which reflects a portion of the ultrasonic waves emitted from the ultrasonic search unit in a direction anterior to the insertion part in order to scan anteriorly of the insertion part; and an optical system for observation located alone a plane passing through a posterior end of the protruding part.

16. An ultrasonic endoscope according to claim 15, wherein the insertion part further includes a channel for treatment device passage through which treatment devices can be inserted, the channel having a delivery port formed at the tip of the insertion part so that a treatment device extended from said delivery port will be located within a scanning area in the anterior direction of the insertion part formed when ultrasonic waves are reflected at the reflector.

17. An ultrasonic endoscope according to claim 16, wherein the scanning area in the anterior direction of the insertion part is formed alone a plane defined by shifting a straight line which intersects the center of the delivery part and a point approximately at the center of the reflection plane in the direction of the longitudinal axis of the insertion part.

18. An ultrasonic endoscope according to claim 16, wherein the protruding part is formed so as to protrude from an area corresponding to no more than one-half the distal end face of the tip of the insertion part.

19. An ultrasonic endoscope according to claim 18, wherein the optical system for observation and delivery port are arranged on the opposite half of the distal end face with respect to the protruding part.

20. An ultrasonic endoscope according to claim 15, wherein the inside of the tip cap is filled with an ultrasonic wave transmission medium which transmits ultrasonic waves.

21. An ultrasonic endoscope according to claim 15, further comprising a balloon removably attached to the tip cap, wherein the balloon is expandable upon being filled with an ultrasonic wave transmission medium.

22. An ultrasonic endoscope according to claim 21, wherein the balloon has a bag shape with an opening at one end thereof.

23. An ultrasonic endoscope according to claim 21, wherein the balloon has a tube shape with openings at both ends thereof.

24. An ultrasonic endoscope according to claim 22, wherein the tip cap includes a groove formed at the proximal end of the tip cap, the openings of the balloon being attached to the tip cap at the grooves.

25. An ultrasonic endoscope according to claim 23, wherein the tip cap includes a groove formed at each of the distal e and the proximal end respectively, of the tip cap, the openings of the balloon being attached to the tip cap at the grooves.

26. An ultrasonic endoscope according to claim 21, wherein the balloon is fitted onto the protruding part and is in an expanded state, the protruding part is positioned within the balloon and a treatment device inserted through the channel and extended from the delivery port is positioned along an exterior surface of the balloon.

27. An ultrasonic endoscope according to claim 15, wherein the ultrasonic search unit is one of a mechanical an electronic scanner.

\* \* \* \* \*